(12) United States Patent
Larsen et al.

(10) Patent No.: US 10,285,789 B2
(45) Date of Patent: *May 14, 2019

(54) DENTAL BLEACHING GELS AND METHODS FOR MAKING AND USING THEM

(75) Inventors: Robert K. Larsen, Sandy, UT (US); Calvin D. Ostler, Riverton, UT (US)

(73) Assignee: CAO Group, Inc., West Jordan, UT (US)

( * ) Notice: Subject to any disclaimer, the term of this patent is extended or adjusted under 35 U.S.C. 154(b) by 1499 days.

This patent is subject to a terminal disclaimer.

(21) Appl. No.: 11/737,597

(22) Filed: Apr. 19, 2007

(65) Prior Publication Data

US 2007/0190483 A1 Aug. 16, 2007

Related U.S. Application Data

(63) Continuation-in-part of application No. 10/797,628, filed on Mar. 10, 2004, now abandoned.

(51) Int. Cl.
| | | |
|---|---|---|
| *A61Q 11/00* | (2006.01) | |
| *A61C 19/06* | (2006.01) | |
| *A61C 17/00* | (2006.01) | |
| *A61C 19/10* | (2006.01) | |
| *A61C 5/62* | (2017.01) | |

(52) U.S. Cl.
CPC .......... *A61C 19/063* (2013.01); *A61C 19/066* (2013.01); *A61C 5/62* (2017.02); *A61C 17/005* (2013.01); *A61C 19/10* (2013.01)

(58) Field of Classification Search
CPC ... A61C 19/063; A61C 19/066; A61C 17/005; A61C 19/10; A61C 5/62
See application file for complete search history.

(56) References Cited

U.S. PATENT DOCUMENTS

| | | | | |
|---|---|---|---|---|
| 3,337,466 | A | * | 8/1967 | Puetzer et al. ................ 510/102 |
| 4,592,487 | A | * | 6/1986 | Simon ..................... A61K 8/20 |
| | | | | 222/94 |
| 5,392,947 | A | * | 2/1995 | Gentile ......................... 220/665 |
| 5,449,509 | A | * | 9/1995 | Jackson et al. ................. 424/49 |
| 5,607,681 | A | * | 3/1997 | Galley et al. ................. 424/405 |
| 5,928,628 | A | * | 7/1999 | Pellico ............................ 424/49 |
| 6,251,386 | B1 | * | 6/2001 | Johansen .................... 424/94.4 |
| 2002/0028754 | A1 | * | 3/2002 | Johansen et al. ............ 510/302 |
| 2004/0062723 | A1 | * | 4/2004 | Zaidel et al. ................... 424/53 |

* cited by examiner

*Primary Examiner* — Lezah Roberts

(57) ABSTRACT

The addition of the Iodide ion by way of Potassium Iodide to a peroxide such as Hydrogen Peroxide in a basic medium yields Free Radical Oxygen and water; generating large amounts of heat and depleting the Hydrogen Peroxide in a matter of minutes. The Free Radical Oxygen generated in this reaction can be utilized to oxidize organic molecules that produce offending stains on select items, including teeth. Once the Free Radical Oxygen has oxidized the offending molecule the color is lost and the solubility changes allowing the colorless oxidized fragments of the offending molecule to be washed away in the solvent. The Iodide ion catalyzes the reaction allowing for precise control over the speed at which the stain is removed without the need for other expensive, cumbersome energy adding equipment such as lights, lasers, heat sources, etc.

6 Claims, 6 Drawing Sheets

DENTAL BLEACHING GELS AND METHODS FOR MAKING AND USING THEM

CROSS-REFERENCES TO RELATED APPLICATIONS

This patent application is a Continuing-in-Part Application and claims benefit to and the priority of its parent, U.S. Utility patent application Ser. No. 10/797,628 filed on Mar. 10, 2004 which is hereby incorporated by reference in its entirety.

FIELD OF THE INVENTION

The present invention relates to the field of bleaching gels used in dentistry and more particularly relates to bleaching gels utilizing a combination of iodide and hydrogen peroxide in a generally basic medium.

BACKGROUND OF THE INVENTION

Bleaching gels for tooth whitening are known in the prior art. Many of these gels utilize a peroxide of some form to bleach stains off of teeth, both natural and artificial. It should be noted that the term "teeth" or "tooth" as used in this specification and the appended claims includes both natural and artificial teeth. This goal is accomplished because peroxides tend to be unstable and have a number of free-radical oxygen atoms which bind with the compounds and elements within staining material, thereby breaking up the stain on an atomic level and removing it. Various methods of improving peroxide performance are also known in the prior art, as anything that will stimulate free-radical oxygen production will generally improve basic performance of a bleaching product. The use of iodine, in particular potassium iodide, with hydrogen peroxide is also known in the field of antiseptics. The use of the hydrogen peroxide as an astringent and the iodine as an antiseptic provide a useful combination when treating minor cut and abrasions. These combinations rely on the disinfecting power of the iodine for their utility, and prefer that the iodine is active and present. This occurs in an acidic environment and leaves the resultant solution of iodine and hydrogen peroxide with the all too familiar reddish-brown staining color associated with antiseptic iodine. There is even some prior art that suggests the use of potassium iodide and peroxide as a cleaner for contact lenses, which requires a pH above 6 in order to limit the iodine coloration, but this still relies on the iodine as a disinfectant and is stated to be used in a preferred pH range of around 7. Starting at a level of approximately 7.5 pH, the relation between tri-iodide molecules and oxygen radicals in the solution changes as the iodine is kept bound in solution as a catalyst and more radicals are released. While it is known that $O_2$ is formed from the reaction, free-radical Oxygen production from the reaction has been, at best, ignored. The parent Application has gone into extensive detail in the prior art and the reader is directed to that discussion, which has already been incorporated by reference above.

The present invention, in its preferred embodiment, is a bleaching gel for teeth presented in a binary solution system, utilizing potassium iodide as a catalyst for generation of free-radical oxygen. The gel is kept in a binary solution, having two separate components that are combined when desired to be used.

The present invention represents a departure from the prior art in that the bleaching gels of the present invention utilize iodide, which precipitates to the stain-causing elemental form at acidic pH levels, as a catalyst for creating bleaching oxygen radicals in peroxides, thereby increasing whitening effectiveness.

SUMMARY OF THE INVENTION

In view of the foregoing disadvantages inherent in the known types of bleaching gels, this invention provides an improved bleaching gel with greater efficiency. To accomplish these objectives, the bleaching gel, in its most basic embodiment, comprises a peroxide based active component and an iodide based catalyst that are kept separate until use.

The more important features of the invention have thus been outlined in order that the more detailed description that follows may be better understood and in order that the present contribution to the art may better be appreciated. Additional features of the invention will be described hereinafter and will form the subject matter of the claims that follow.

Many objects of this invention will appear from the following description and appended claims, reference being made to the accompanying drawings forming a part of this specification wherein like reference characters designate corresponding parts in the several views.

Before explaining at least one embodiment of the invention in detail, it is to be understood that the invention is not limited in its application to the details of construction and the arrangements of the components set forth in the following description or illustrated in the drawings. The invention is capable of other embodiments and of being practiced and carried out in various ways. Also it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods, and systems for carrying out the several purposes of the present invention. It is important, therefore, that the claims be regarded as including such equivalent constructions insofar as they do not depart from the spirit and scope of the present invention.

DETAILED DESCRIPTION OF THE PREFERRED EMBODIMENT

With reference now to the drawings, the preferred embodiment of the bleaching gels are herein described. It should be noted that the articles "a", "an", and "the", as used in this specification, include plural referents unless the content clearly dictates otherwise.

Figure 1:
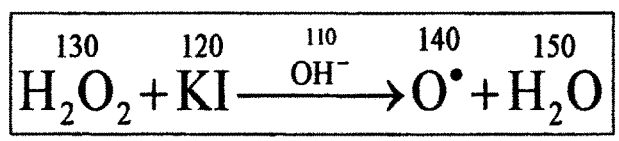
FIG. 1 is a depiction of the bleaching, or whitening, reaction.
Figure 1:
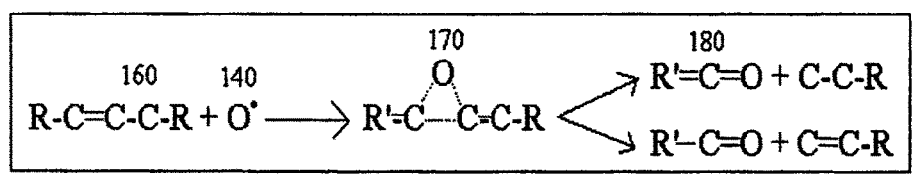

With reference to FIG. 1, it is well established that the free radical oxygen atoms (140) liberated from peroxides such as hydrogen peroxide (130), carbamide peroxide, and salts of peroxides formed from the alkali and alkaline earth metals, readily attack and oxidize organic molecules (160) that comprise the stains in discolored teeth. It is also well established that a release of free radical oxygen atoms from the peroxides can be accelerated by the addition of heat, light and/or chemicals; specifically chemicals that raise the pH of the peroxide environment. A lengthy dissertation of the exact mechanisms is discussed in prior work found in U.S. Pat. No. 6,116,900, "Binary energizer and peroxide delivery system for dental bleaching" which is herein incorporated by reference.

For whitening and bleaching purposes, the addition of the Iodide ion by way of Potassium Iodide (120) to a peroxide such as Hydrogen Peroxide (130) in a basic medium (110) yields Free Radical Oxygen (140) and water (150); generating large amounts of heat and depleting the Hydrogen Peroxide fairly rapidly given a set relative amount of iodide in the system. The Free Radical Oxygen (140) generated in this reaction can be utilized to oxidize organic molecules that produce offending stains (160) on select items, including teeth. Once the Free Radical Oxygen has oxidized the offending molecule (170) the color is lost and the solubility changes allowing the colorless oxidized fragments (180) of the offending molecule to be washed away in the solvent.

It should be noted that earlier uses of iodine and peroxide were antiseptic in nature and utilized free iodine. The uses of these compositions required the medium to have pH in a neutral to acidic ranges, as free iodine is eliminated as pH is raised to a basic range, beginning somewhere between a pH of 6.5 and 7.5. This invention does not use free iodine. In the basic range, in particular 7.5 and above, the peroxide decomposition yields a large number of oxygen free radicals in a short period of time while free iodine is eliminated. This combination is especially effective in bleaching applications. As such, any free iodine left in solution is of a negligible amount and not considered relevant to the invention Ideally, the composition should be thickened into a gel form. The term "gel" is defined in this document, as a product that, when applied to the teeth and will tend to adhere to the teeth rather than immediately running off in order to aid in providing a whitening treatment. Therefore the "gel" could also be a thick paste or a very runny or "loose gel." A gel may be created with or without a thickener or viscosity increaser. The exact formulations for various gels has been exhaustively studied and reported. Any gel that is stable can be utilized. Examples of gelling materials include but are not limited to the long list of polyacrylic acid thickeners most commonly sold under the trade name Carbopol by the BF Goodrich Company; the gum thickeners such as guar gum and xanthane gum; the cellulose thickeners such as methyl cellulose, sodium carboxymethyl cellulose, hydroxyethyl cellulose, hydroxpropyl methyl cellulose and hydroxymethyl propyl cellulose; glycerin and its derivatives; the silica thickeners such as fumed silica and silica aerogel thickener; glycol and its many derivatives such as propylene glycol, polyethylene glycol, and polypropylene glycol; polyoxyethylene polyoxypropylene block copolymeric thickeners available under the trade name PLURONIC available from BASF, cross-linked copolymers of acrylic acid and a hydrophobic comonomer available under the trade name PEMULEN from the BF Goodrich Company, and other thickeners such as sorbitol and polyvinyl alcohol. Polyvinylpyrrolidone is particularly attractive as it provides a gel that is stable across a wide range of pH values. Polyvinylpyrrolidone is also an iodophor. An iodophor is any surface active agent or polymer that acts as carriers and solubilizing agents for iodine. Virtually any thickener may be used provided that it is safe for human exposure and stable in the environments. All of these thickening agents are readily available from the standard chemical sources such as Sigma-Aldrich of Milwaukee, Wis. and Spectrum Chemicals of Gardena Calif. Examples of gels are provided in the parent application referenced above and are specifically incorporated here by reference.

Figure 2:
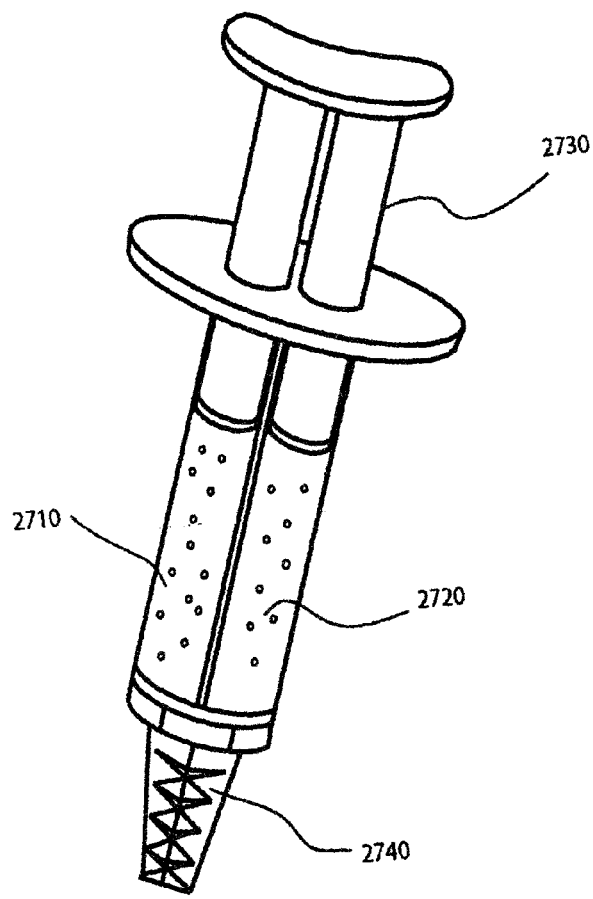
FIG. 2 depicts a double barrel syringe delivery mechanism for mixing and delivering a two-part bleach or whitener.

The delivery mechanism and method can be any system that keeps the two components separate until immediately prior to use. Maintaining separation of the two components is necessary as the reaction between the peroxide and iodide will deplete the peroxide too rapidly for the composition to be manufactured, shipped, and stored as a combined solution. Delivery mechanisms can be as simple as two separate containers in which appropriate amounts of each component are removed, placed into a mixing dish, mixed, and then applied to the teeth. For convenience they can include various two component dispensers that automatically dispense appropriate amounts of both components when force is applied such as the double barrel syringe as illustrated in FIG. 2. In such a delivery system the peroxide containing component is maintained in its own chamber (2710) which is isolated from the non-peroxide containing component which is in its own chamber (2720). When force is applied to the plungers of the syringe (2730) the two phases are forced out of their chambers and may pass through an auto-mixing tip (2740) for added convenience. However, an auto-mixing tip is not required; the consumer could manually mix the two components after they are expressed from their respective chambers.

Figure 3:
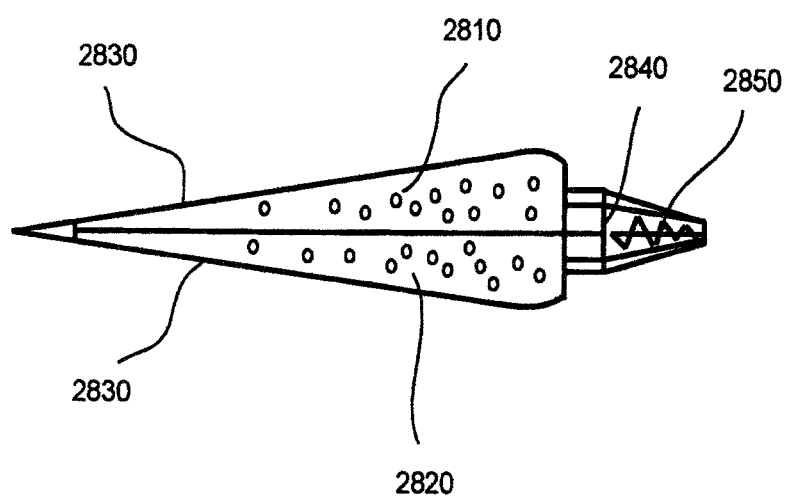
FIG. 3 depicts a two-chambered collapsible tube mixing and delivery system for a two-part bleach or whitener.

Alternatively, the delivery system could consist of a two chambered, collapsible tube as is illustrated in FIG. 3. In such a configuration the peroxide containing component is contained in its own chamber (2810) which is isolated from the camber containing the non-peroxide component (2820). When force is applied to the walls of the collapsible tube (2830) the components are forced out of their respective chambers and may pass through an auto-mixing (2840) for added convenience. However, an auto-mixing tip is not required; the consumer could manually mix the two components after they are expressed from their respective chambers.

Figure 4:
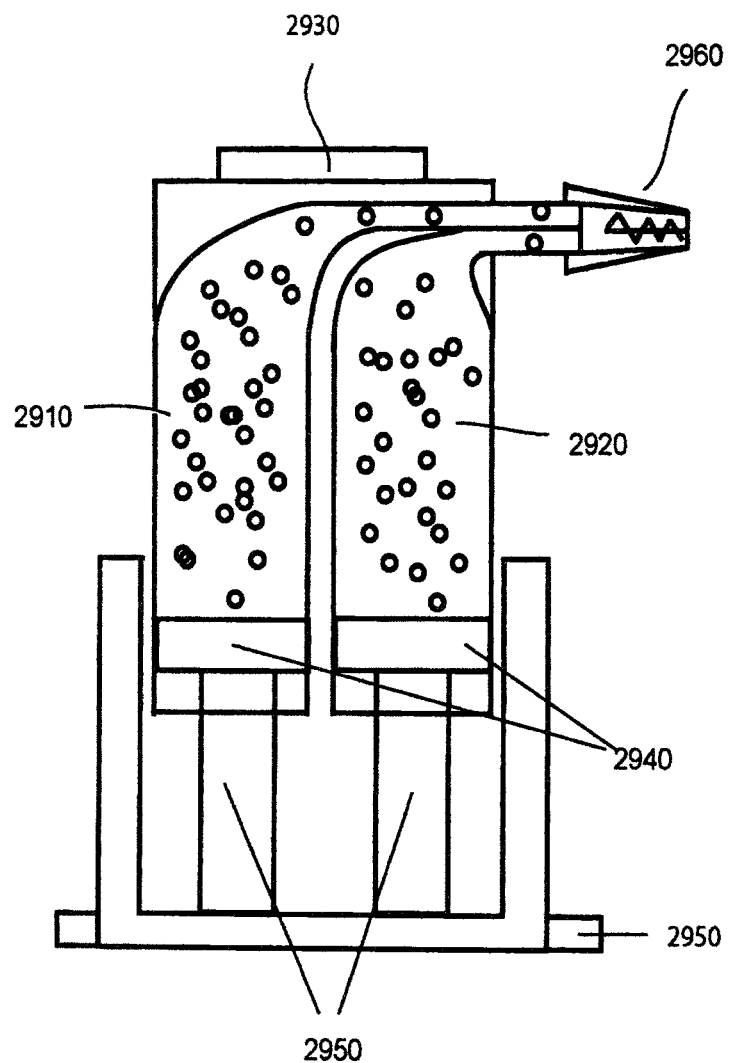
FIG. 4 depicts a rigid two-chambered canister mixing and delivery system for a two-part bleach or whitener.

Alternatively, the delivery system could consist of a canister with rigid components as is illustrated in FIG. 4. In such a configuration the peroxide containing component is contained in its own chamber (2910) which is isolated from the camber containing the non-peroxide component (2920). When force is applied to the top of the chamber (2930), the force is transferred to the moving seals (2940) by way of the immovable posts (2950) which are integral with the base of the unit (2955) which would be resting on a solid surface such as a countertop. As the force is applied, the components are forced out of their respective chambers and may pass through an auto-mixing (2860) for added convenience. However, an auto-mixing tip is not required; the consumer could manually mix the two components after they are expressed from their respective chambers. Many other systems are possible. The above examples are offered for illustrative purposes and are not intended to limit the delivery systems to the offered examples.

Figure 5:
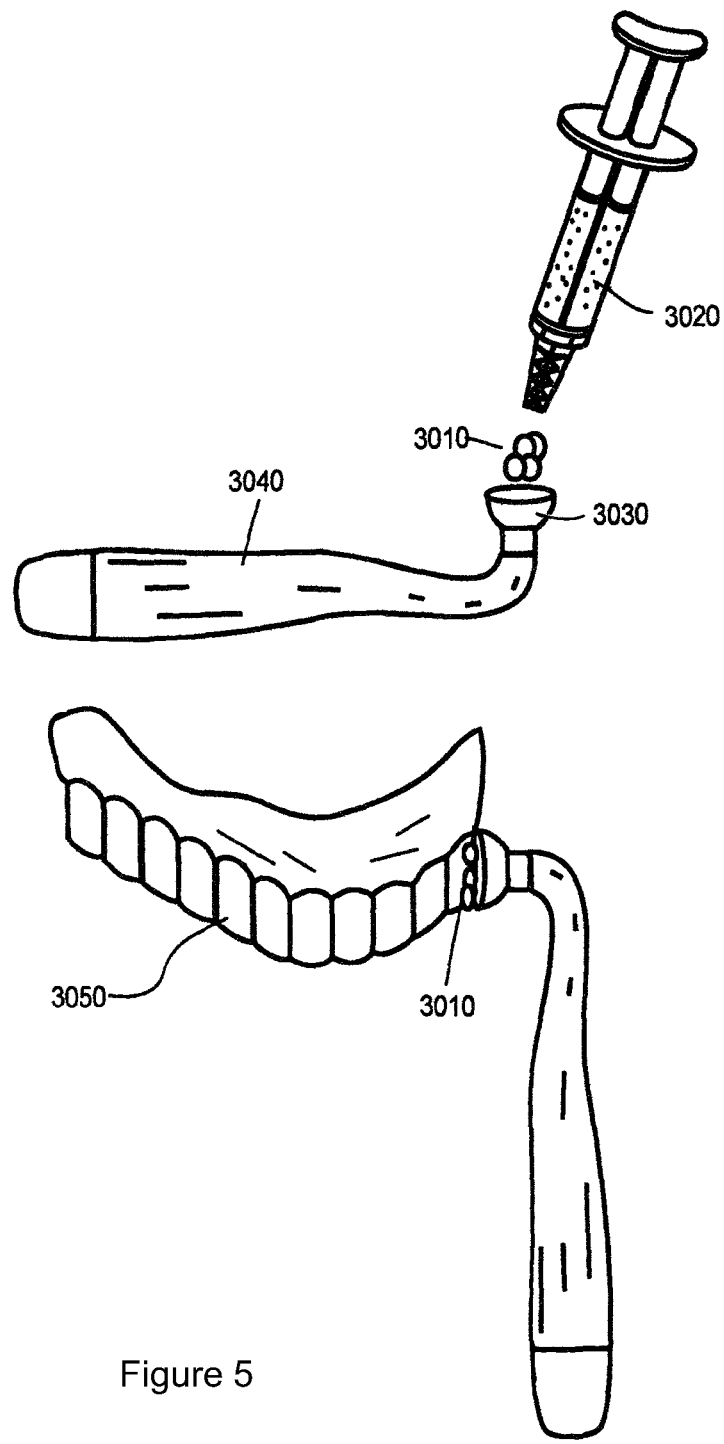
FIG. 5 depicts the steps of mixing and dispensing a bleach onto a dental applicator and applying the bleach to teeth.

The resultant mixture of the two bleach components into a powerful and effective bleach or whitener can be applied to the teeth by a dentist or directly by the consumer in many different ways. For instance the dentist, refer to FIG. 5, could apply the mixture (3010) to a prophy cup (3030) from a dispensing device, in this case a double barreled syringe (3020). The prophy cup would be attached to and driven by a dental hand piece (3040). The mixture (3010) would then be applied, by the dentist, to the consumer's teeth (3050).

Figure 6:
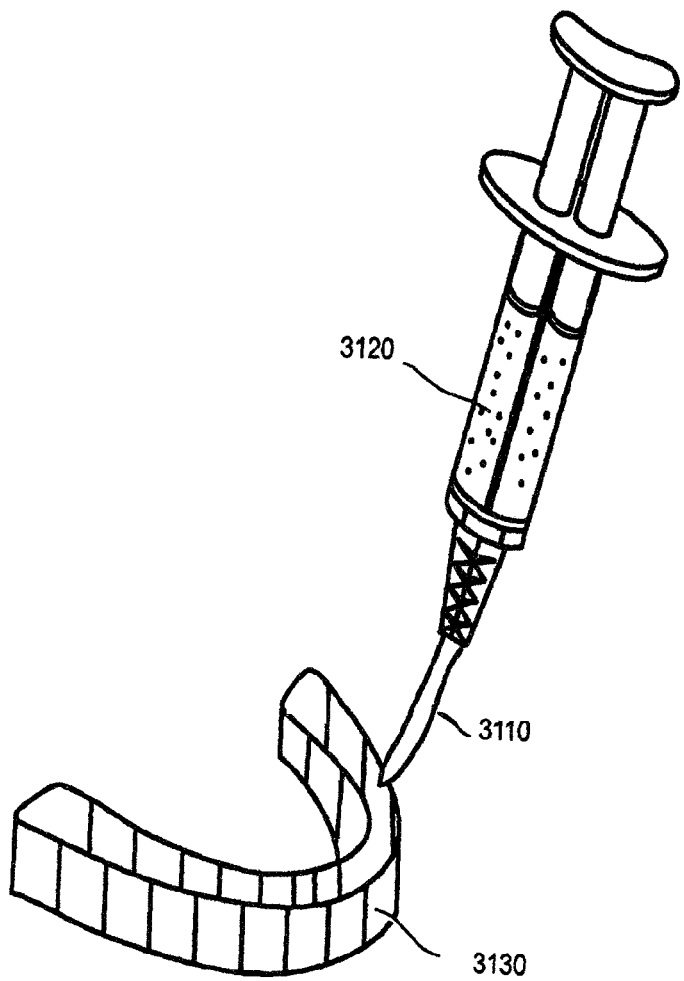
FIG. 6 depicts the steps of mixing and dispensing a bleach into a dental tray such as a patient may wear during the night hours for a whitening effect.

Alternatively, the consumer could apply the mixture themselves by way of the now popular "night guard" tray method as is illustrated in FIG. 6. The mixture (3110) would be extruded, by the consumer, from a dispensing device, in this case a double barrel syringe (3120) into the tray (3130). The consumer would then place the tray (3130) and mixture (3120) on their teeth according to the directions of the manufacturers. Other application techniques, such as application by a toothbrush, are possible. The above examples are offered for illustrative purposes and are not intended to limit the application techniques to the offered examples.

Although the present invention has been described with reference to preferred embodiments, numerous modifications and variations can be made and still the result will come within the scope of the invention. No limitation with respect to the specific embodiments disclosed herein is intended or should be inferred.

What is claimed is:

1. A system for bleaching teeth, the system comprising:
   a. a vessel, said vessel being a collapsible tube comprising two chambers, both with selectable fluid communication with an auto-mixing tip, which is in turn in selectable fluid communication with a dispensing means;
   b. a catalyst component being in gel form and containing an iodide ion, stored in one chamber; and
   c. a bleaching component being in gel form and containing peroxide, stored in the other chamber; wherein:
      the system is stored with the two chambers having no fluid communication with the auto-mixing tip;
      the system is used by establishing fluid communication between the two chambers and the auto-mixing tip allowing the catalyst component and the bleaching component to mix to form a chemical reaction system that produces a bleaching composition;
      the system has a pH over 7.5;
      the iodide ion serves as an unconsumed catalyst within the reaction system and free iodine is not a product of the reaction system; and
      the bleaching composition is dispensed through the dispensing means; and
      wherein the composition is a powerful and effective teeth whitener when mixed.

2. The system of claim 1 having a pH between 8 and 9, inclusively.

3. The system of claim 1, the peroxide being hydrogen peroxide.

4. The system of claim 1, the iodide ion being in the form of potassium iodide.

5. The system of claim 1, the iodide ion being in the form of potassium iodide and the peroxide being hydrogen peroxide.

6. The system of claim 5 having a pH between 8 and 9, inclusively.

* * * * *